United States Patent [19]
Sakai et al.

[11] Patent Number: 5,192,499
[45] Date of Patent: Mar. 9, 1993

[54] FLUID PROCESSING APPARATUS AND ARTIFICIAL LUNG

[75] Inventors: Satoru Sakai, Kanagawa; Kiyohide Ishikawa, Shizuoka, both of Japan

[73] Assignee: Terumo Kabushiki Kaisha, Tokyo, Japan

[21] Appl. No.: 551,942

[22] Filed: Jul. 12, 1990

[30] Foreign Application Priority Data

Jul. 14, 1989 [JP] Japan .................................. 1-183499

[51] Int. Cl.$^5$ ........................ A61M 1/03; A61M 1/16; A61M 1/36
[52] U.S. Cl. ............................... 422/46; 422/48; 261/DIG. 28; 128/DIG. 3; 210/321.8; 210/450; 210/321.89; 210/500.23; 165/46; 165/158; 165/905; 165/906
[58] Field of Search ................. 165/905, 173, 70, 46, 165/158, 906; 210/321.8, 321.89, 450, 500.23; 128/DIG. 3; 261/DIG. 28; 422/46, 48

[56] References Cited

U.S. PATENT DOCUMENTS

| | | | |
|---|---|---|---|
| 1,810,286 | 6/1931 | MacPhee | 165/70 |
| 3,489,209 | 1/1970 | Johnson | 165/905 |
| 4,586,566 | 5/1986 | Kern et al. | 165/905 |
| 5,058,661 | 10/1991 | Oshiyama | 165/905 |

FOREIGN PATENT DOCUMENTS

| | | |
|---|---|---|
| 0081118 | 6/1983 | European Pat. Off. |
| 0109789 | 6/1984 | Japan ................................ 165/905 |

*Primary Examiner*—John K. Ford
*Attorney, Agent, or Firm*—Frishauf, Holtz, Goodman & Woodward

[57] ABSTRACT

The fluid processing apparatus of the present invention comprises a housing having a first fluid inlet and a first fluid outlet; a fluid processing tubular means received in the housing; partitions securing the opposed ends of the fluid processing tubular means to the housing in a fluid tight seal to partition the housing interior into a first fluid chamber in fluid communication with the first fluid inlet and the first fluid outlet and a second fluid chamber defined in the fluid processing tubular means; a second fluid inlet and a second fluid outlet in fluid communication with the second fluid chamber; and projections formed on an inner surface of one end portion of the housing so as to project toward the nearer end opening of the housing, said partition of the one end portion side of said housing being secured to the one end portion of the housing so that the projections are positioned within the partition. Therefore, if a large annular portion where the fluid processing tubular means is not present is formed in the end portion of the housing, because the projections are positioned in the annular portion of the partition, shrinkage of the potting composition forming the partition is suppressed and any separation between the partition and the inner surface of the housing due to the shrinkage of the potting composition is prevented. Further, it is also prevented to form a weak bond portion between the partition and the inner surface of the housing.

14 Claims, 5 Drawing Sheets

5,192,499

FLUID PROCESSING APPARATUS AND ARTIFICIAL LUNG

BACKGROUND OF THE INVENTION

This invention relates to a fluid processing apparatus. More particularly, it relates to a fluid processing apparatus for processing blood, for example, to a heat exchanger for regulating the temperature of blood, an artificial lung for gas exchange in blood, a plasma separator or the like.

There is hither to known a heat exchanger in which is provided heat-exchange tubular means in the form of, for example, a plurality of heat-exchange fine tubes or a coiled tube. Also in an artificial organ such as an artificial lung, material-exchange fine tubes are provided. They are gas-exchange hollow fibers in an artificial lung or dialysis hollow fibers in an artificial kidney.

The above heat exchanger or artificial organ is used in the manner that blood is passed through the heat or material-exchange tubular means while a heat or material-exchange medium is passed between the tubular means and the housing.

In those apparatus, the heat or material-exchange tubular means is secured to the housing in a fluid tight seal by applying a potting composition, for example, a polyurethane base potting composition to form a partition.

However, there is the possibility that the potting composition forming the partition will shrink with time. The potting composition thus peels off the inner surface of the housing due to the shrinkage and thus does not maintain the fluid tight seal established during manufacturing.

Particularly, the shrinkage of the potting composition tends to occur at the periphery of the partition where the heat or material-exchange tubular means is not present. The reason is that the shrinkage of the potting composition is suppressed by the tubular means in the area where the heat or material-exchange tubular means is present while the suppression of the shrinkage is not effected in the area where the heat or material-exchange tubular means is not present. For this reason, for example, in the case of a heat exchanger in which the end of the housing is spread for connecting it to another fluid processing apparatus and which has a large annular area where the heat exchange tubular means is not present, there is the good possibility that the partition will peel off the inner surface of the housing due to shrinkage of the potting composition.

Although the potting composition may not be separated from the inner surface of the housing during a priming operation which is carried out prior to use of a fluid processing apparatus of this kind, there is the possibility that a weak bond portion is formed due to a shrinkage of the potting composition. If an impact is subsequently accidentally applied to such an apparatus when blood is passed therethrough for, for example, heat exchange, there is the risk that the partition well peel off the housing. Such a separation between the partition and the housing is very dangerous because heat-exchange fluid such as hot or cool water can mix with blood through the separated gap or crevice.

SUMMARY OF THE INVENTION

Accordingly, it is an object of the present invention to provide a fluid processing apparatus in which a separation between the partition and the inner surface of the housing due to a shrinkage of the potting composition or the formation of a weak bond portion between the partition and the inner surface of the housing is prevented even in the case of a fluid processing apparatus having a large annular area where the fluid processing tubular means is not present.

The above object is attained by a fluid processing apparatus comprising a housing having a first fluid inlet and a first fluid outlet; a fluid processing tubular means received in said housing; partitions securing the opposed ends of said fluid processing tubular means to said housing in a fluid tight seal to partition the housing interior into a first fluid chamber in fluid communication with said first fluid inlet and said first fluid outlet and a second fluid chamber defined in said fluid processing tubular means; a second fluid inlet and a second fluid outlet in fluid communication with said second fluid chamber; and projections formed on an inner surface of one end portion of said housing so as to project toward the nearer end opening of said housing, said partition of the one end portion side of said housing being secured to said one end portion of said housing so that said projections are positioned within said partition.

DETAILED DESCRIPTION OF THE PREFERRED EMBODIMENTS

Figure 1:
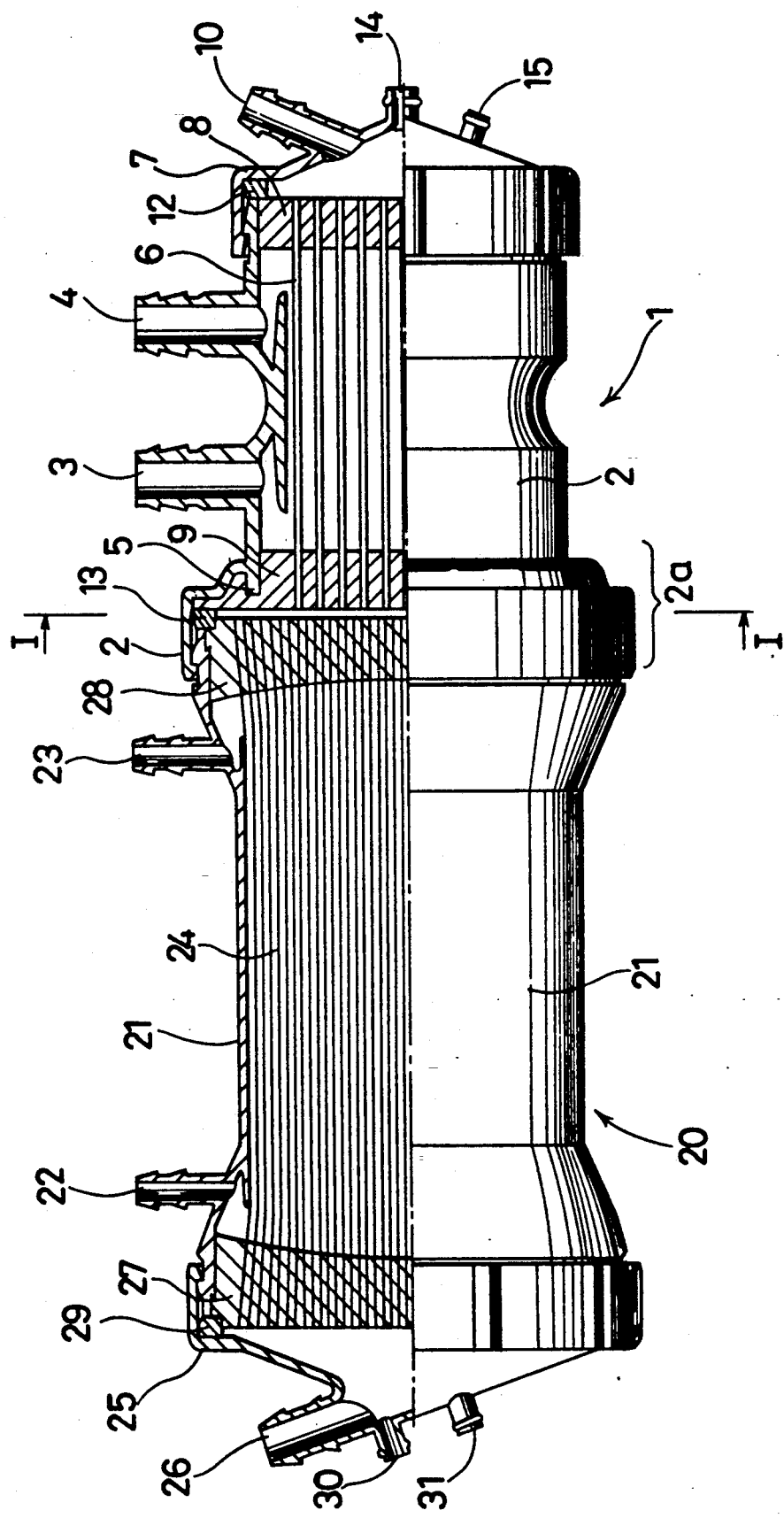
FIG. 1 is a partially cross-sectional side view of an embodiment in which a fluid processing apparatus of the present invention is applied to an artificial lung equipped with a heat exchanger.

A fluid processing apparatus of the present invention will be described with reference to embodiments shown in drawings.

A fluid processing apparatus 1 of the present invention comprises a housing 2 having a first fluid inlet 3 and a first fluid outlet 4; a fluid processing tubular means 6 received in the housing 2; partitions 8 and 9 securing the opposed ends of the fluid processing tubular means 6 to the housing 2 in a fluid tight seal to partition the housing interior into a first fluid chamber in fluid communication with the first fluid inlet 3 and the first fluid outlet 4 and a second fluid chamber defined in the fluid processing tubular means 6; a second fluid inlet 10 and a second fluid outlet in fluid communication with the second fluid chamber; and projections 5 formed on an inner surface of one end portion of the housing 2 so as to project toward the nearer end opening of the housing 2, said partition 9 of the one end portion side of the housing 2 being secured to the one end portion of the housing 2 so that the projections 5 are positioned within the partition 9.

An embodiment in which the fluid processing apparatus of the present invention is applied to an artificial lung equipped with a heat exchanger will be described with reference to FIGS. 1 and 2.

Figure 2:
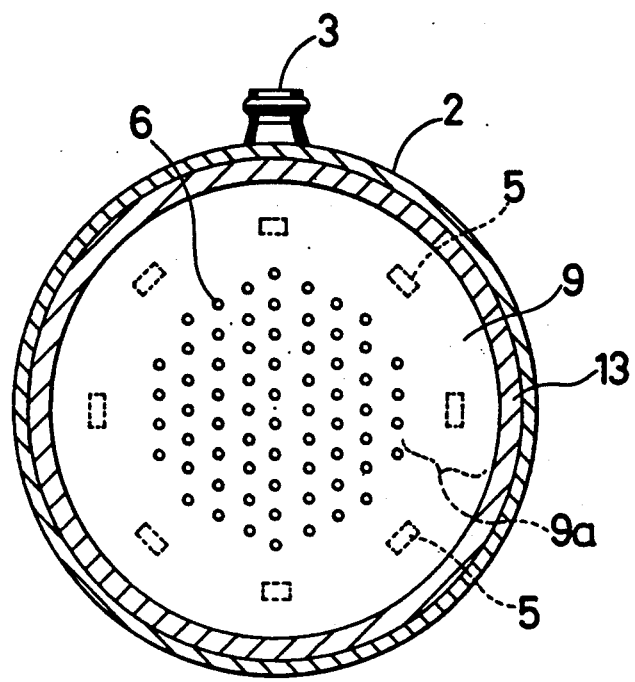
FIG. 2 is a cross section taken along line I—I of FIG. 1.

FIG. 1 is a partially cross-sectional side view of an embodiment in which the fluid processing apparatus is applied to an artificial lung equipped with a heat exchanger and FIG. 2 is a cross section taken along line I—I of FIG. 1.

A heat exchanger 1 to which the fluid processing apparatus of the present invention is applied is attached coaxially with an artificial lung 20.

The heat exchanger 1 includes a tubular housing 2 and a heat-exchange tubular means 6. The fluid processing tubular means is received in the tubular housing 2. The heat-exchange tubular means 6 comprises a large number of heat-exchange fine tubes. Each heat-exchange fine tube is made of metal having a high heat conductivity such as stainless steel, aluminum and copper. It has an inner diameter of 0.5 to 10 mm, preferably 2 to 5 mm. About 10 to about 2,000, preferably about 50 to about 1,000 heat-exchange fine tubes are received in the housing 2. The heat-exchange fine tubes are illustrated as straight tubes in FIG. 1 though they may be spiral tubes.

The opposed ends of the heat-exchange tubular means 6 are secured to the housing 2 through partitions 8 and 9 in a fluid tight manner. The partitions 8 and 9 are made of a high-molecular potting composition such as polyurethane and silicone rubber. The heat-exchange tubular means 6 and the partitions 8 and 9 partition the interior of the housing 2 into the first fluid chamber which is a heat-exchange fluid chamber and the second fluid chamber which is a blood chamber.

The tubular housing 2 is provided with a heat-exchange fluid inlet 3 and a heat-exchange fluid outlet 4.

The housing 2 may be cylindrical or polygonal in configuration. A cylindrical housing is preferred. The housing 2 may be molded from any desired material, for example, polycarbonate, acryl-styrene copolymer and acryl-butylene-styrene copolymer. On the outside of the partition 8 is attached a blood introduction port 7 having a blood inlet 10 in fluid communication with the inner space of the heat-exchange tubular means 6. The blood introduction port 7 is provided with a drug injection port 14 and a blood collection port 15. The blood introduction port 7 is mechanically mounted onto one end portion of the housing 2 by engagement. An O-ring disposed on the inner surface of the blood introduction port 7 comes into close contact with the outside surface of the periphery of the partition 8 to form a fluid tight seal between the blood introduction port 7 and the partition 8.

The blood introduction port 7 may be welded to the housing 2 by ultrasonic or high frequency welding or may be bonded to the housing 2 with an adhesive. Alternatively, it may be fixed to the housing 2 with a fastening ring.

As shown in FIG. 1, the housing 2 has a large-diameter portion 2a at the portion where the partition 9 is disposed. Within the large-diameter portion 2a is provided a plurality of separated projections 5 projecting toward the nearer end opening of the housing 2 as shown in FIGS. 1 and 2. The partition 9 is secured to the inner surface of the large-diameter portion 2a of the housing 2. The projections 5 are positioned within the partition 9. The partition 9 has an annular area 9a at the periphery where the heat-exchange tubular means 6 is not present as shown in FIGS. 1 and 2. The projections 5 are positioned in the annular area 9a.

As described above, even in the case of the heat exchanger 1 having the large-diameter portion 2a and the large annular area 9a where the heat-exchange tubular means 6 is not present, the potting composition is prevented from shrinking because the projections 5 are positioned in the annular area 9a of the partition 9. Thus, any separation between the partition 9 and the inner surface of the housing 2 due to shrinkage of the potting composition is prevented. It is also prevented to form a weak bond portion between the partition 9 and the inner surface of the housing 2.

The partition 9 is preferably formed such that the entirety of the projections 5 is positioned therein. By this construction, if an impact is accidentally applied to the heat exchanger during operation, the impact applied to the projections 5 is absorbed because the entirety of the projections 5 is enclosed in the partition 9. This construction prevents the peeling of the potting composition off the tips of the projections 5.

It is preferred that more than two, more preferably more than four projections 5 are disposed nearly at regular intervals as shown in FIG. 2. It is also preferred that the projections 5 are present at 1/30 to 1/1.5 of the periphery of the annular area where the projections 5 are disposed. The projections 5 are dispersed in an annular area. In the area where the projections 5 are not present, the potting composition forming the partition 9 is not prevented from flowing in the housing 2 by the projections 5. The projections 5 are preferably located in the intermediate portion between the inner surface of the large-diameter portion 2a of the housing 2 and the circle formed by the outermost tubes of the heat-exchange tubular means 6 as shown in FIG. 2. By this arrangement, shrinkage of the potting composition is effectively suppressed.

The shape of the projections 5 is not limited to that shown in FIG. 2. For example, it may be circular, elliptic, polygonal, star-shaped, etc. in its cross section. It is preferred that the projections 5 have contact area with the partition 9 as large as possible. For this purpose, a large number of small projections may be formed on the surface of the projections 5 or the surface of the projections 5 may be roughened. It is also preferred that the inner surface of the housing have a contact area with the partition 9 as large as possible. For this purpose, a large number of small projections may be formed on the inner surface of the housing 2 in contact with the partition 9 or the inner surface of the housing 2 in contact with the partition 9 may be roughened.

The heat-exchange tubular means 6 is open at the end of the partition 9. A blood outlet which is the second fluid outlet is formed by the entirety of the heat-exchange tubular means 6 at the end of the partition 9. The end of the large-diameter portion 2a of the housing 2 is mechanically fitted to one end of a housing 21 of the artificial lung 20. The partition 9 of the heat exchanger 1 faces a partition 28 of the artificial lung 20. An O-ring 13 makes a fluid tight seal between the heat exchanger 1 and the artificial lung 20.

The artificial lung 20 comprises a tubular housing 21, an assembly of gas-exchange hollow fibers 24 received in the tubular housing 21, and partitions 27 and 28 to which the opposed ends of the hollow fibers 24 are secured in a fluid tight seal. The interior of the tubular housing 21 is divided into a blood chamber and a gas chamber. The tubular housing 21 is provided with a gas inlet 22 and a gas outlet 23 in fluid communication with the gas chamber. On the outside of the partition 27 at the end of the tubular housing 21, there is disposed a cap-like blood discharge port 25 having a blood outlet 26 in fluid communication with the inner spaces of the hollow fibers 24.

Each hollow fiber 24 consists of a porous membrane having an inner diameter of 100 to 1,000 μm, a wall thickness of 5 to 200 μm, preferably 10 to 100 μm, and a porosity of 20 to 80%, preferably 30 to 60%, with pores having diameters of 0.01 to 5 μm, preferably 0.01 to 1 μm. About 5,000 to 100,000 hollow fibers are received in the housing 21 in parallel with the axis of the housing 21. The porous membrane of each hollow fiber is made of a hydrophobic polymeric material such as polypropyrene, polyethylene, polysulfone, polyacrylonitrile, polytetrafluoroethylene, and cellulose acetate. The porous membrane is preferably made of a polyolefinic resin, and most preferably polypropylene. The membrane is preferably formed from such a resin by a drawing or solid-liquid phase separation technique such that the membrane has pores formed in its wall.

Figure 4:
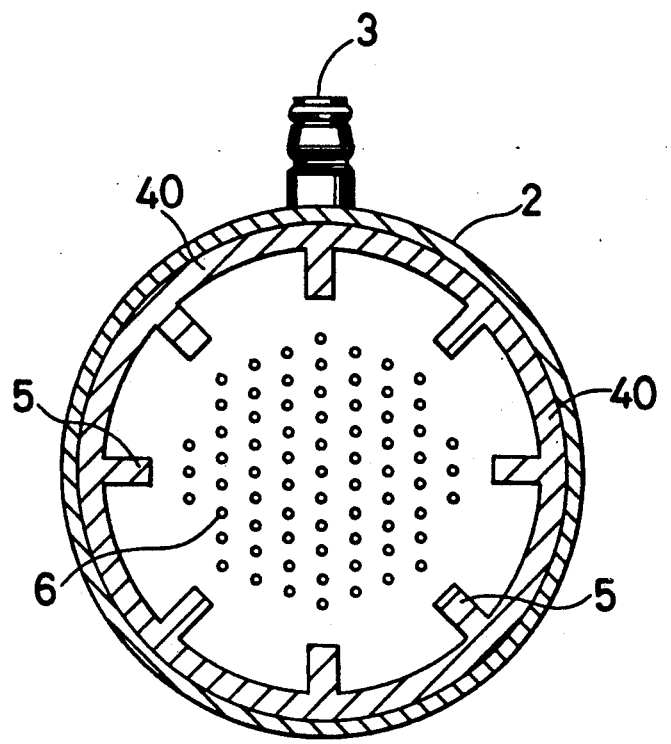
FIG. 4 is a cross section taken along line II—II of FIG. 3.
Figure 3:
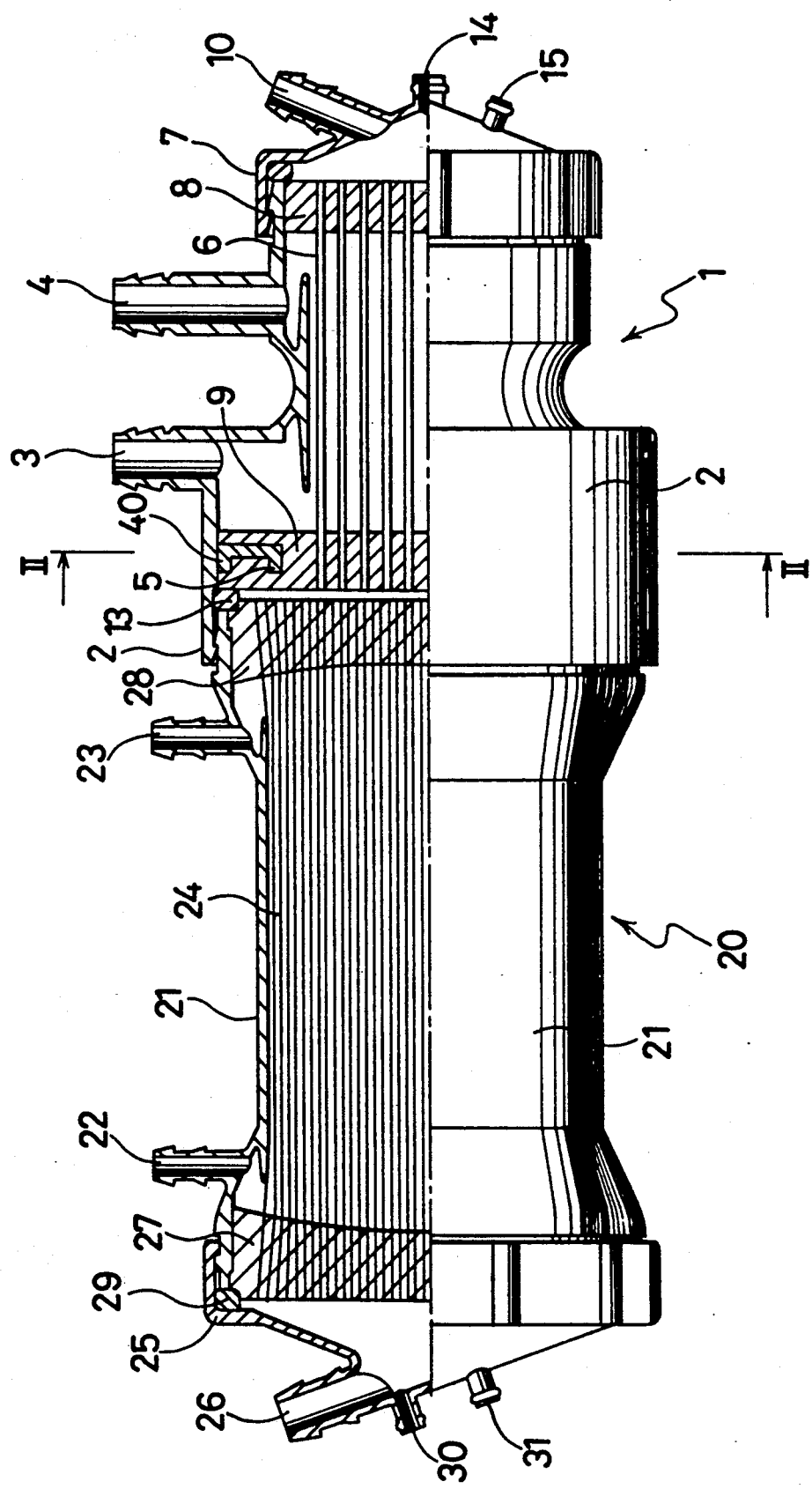
FIG. 3 is a partially cross-sectional side view of another embodiment in which a fluid processing apparatus of the present invention is applied to an artificial lung equipped with a heat exchanger.

Next, an embodiment shown in FIGS. 3 and 4 will be described.

The difference between this embodiment and the embodiment shown in FIG. 1 is in the shape of the housing 2 and the configuration of the projections 5. Specifically, in the heat exchanger 1 of this embodiment, the large-diameter portion is not formed only at the end of the housing 2 but the housing 2 comprises a small-diameter tubular portion on the right side of the center of the housing 2 and a large-diameter tubular portion on the left side thereof. The large-diameter tubular portion on the left side of the center of the housing 2 has a constant inner diameter. No larger-diameter portion is formed therein. An annular member 40 including projections 5 is inserted in and fixed to the large-diameter tubular portion. The annular member 40 has eight projections extending in the radial direction toward the center of the annular member 40 as shown in FIG. 3 and FIG. 4 which is a cross section taken along line II—II of FIG. 3. The eight projections are arranged at regular intervals. The tip end of each of the eight projections is bent toward the nearer end opening of the housing 2 to constitute each projection 5 as shown in FIG. 3. The annular member 40 is embedded in the partition 9 as shown in FIG. 3. The construction of this embodiment except the housing 2 and the projections 5 is the same as that of the embodiment shown in FIGS. 1 and 2.

Figure 5:
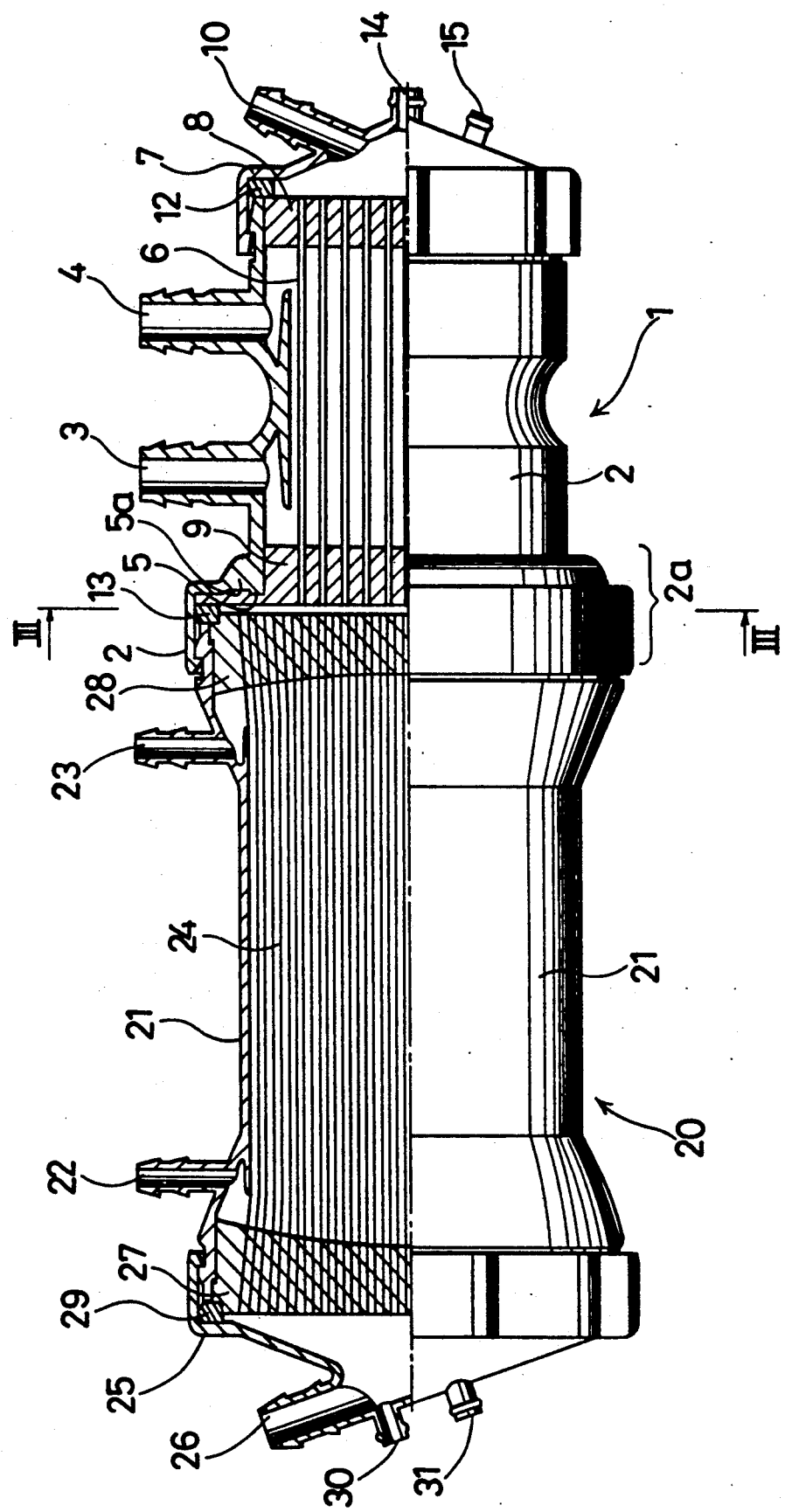
FIG. 5 is a partially cross-sectional side view of another embodiment in which a fluid processing apparatus of the present invention is applied to an artificial lung equipped with a heat exchanger.
Figure 6:
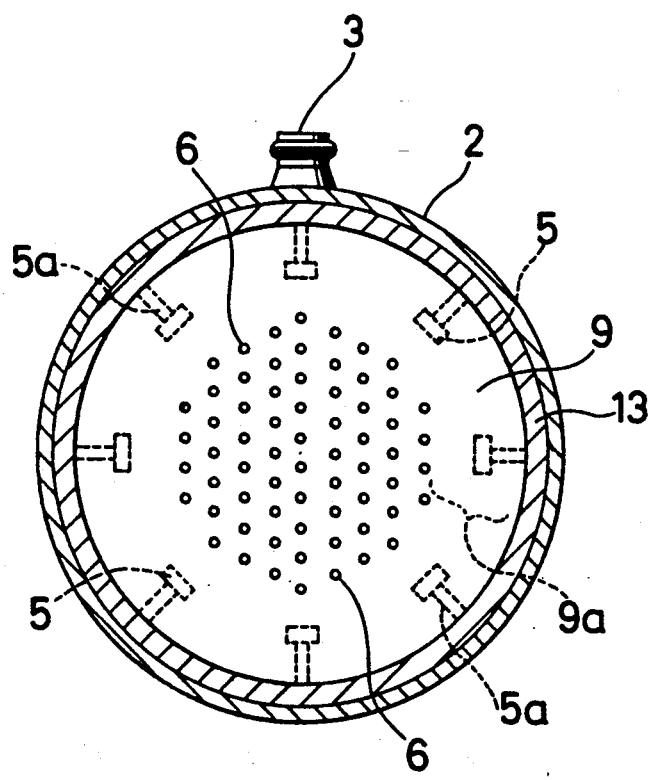
FIG. 6 is a cross section taken along line III—III of FIG. 5.

Next, an embodiment shown in FIGS. 5 and 6 will be described.

This embodiment differs from the embodiment shown in FIG. 1 in the configuration of the projections 5. Specifically, in the heat exchanger 1 of this embodiment, the projections 5 formed in the heat exchanger housing 2 have reinforcement portions 5a. Each reinforcement portion connects a part of a side surface of the projection 5 on the inner surface side of the housing 2 to the inner surface of the housing 2 as shown in FIG. 5 and FIG. 6 which is a cross section taken along line III—III of FIG. 6. The reinforcement portion 5a prevents the projection 5 from deforming toward the center of the housing 2 due to the shrinkage of the potting composition of the partition 9. Therefore, it can more effectively prevents separation of the partition 9 from the inner surface of the housing 2 due to the shrinkage of the partition 9.

Although the fluid processing apparatus of the present invention has been described as being applied to a heat exchanger, it is also applicable to other artificial organ such as an artificial lung itself and an artificial kidney. Further, the fluid processing apparatus of the present invention is also applicable to a plasma separator.

The fluid processing apparatus of the present invention is set in an extracorporeal circuit. For example, in an artificial lung equipped with a heat exchanger, blood introduced from the blood inlet 10 of the heat exchanger 1 flows in the heat-exchange tubular means 6 while hot or cool water introduced from the heat-exchange fluid inlet 3 of the housing 2 flows between the housing 2 and the heat-exchange tubular means 6. The blood is thus warmed or cooled and then flows out through the blood outlet formed by the entirety of the end of the tubular means 6. The blood then flows in the hollow fibers 24 through the blood inlet formed by the entirety of the end of the hollow fibers 24 which are open in the partition 28 of the artificial lung 20. On the other hand, oxygen-containing gas enters the artificial lung 20 from the gas inlet 22 of the housing 21 of the artificial lung 20. The blood comes into contact with the oxygen-containing gas through the hollow fibers 24 so that carbon dioxide is removed from and oxygen is added to the blood. The blood then flows out through the blood outlet 26.

The fluid processing apparatus of the present invention comprises a housing having a first fluid inlet and a first fluid outlet; a fluid processing tubular means received in said housing; partitions securing the opposed ends of said fluid processing tubular means to said housing in a fluid tight seal to partition the housing interior into a first fluid chamber in fluid communication with said first fluid inlet and said first fluid outlet and a second fluid chamber defined in said fluid processing tubular means; a second fluid inlet and a second fluid outlet in fluid communication with said second fluid chamber; and projections formed on an inner surface of one end portion of said housing so as to project toward the nearer end opening of said housing, said partition of said one end portion side of said housing being secured to said one end portion of said housing so that said projections are positioned within said partition. Therefore, if a large annular portion where the fluid processing tubular means is not present is formed in the end portion of the housing, because the projections are positioned in the annular portion of the partition, shrinkage of the potting composition forming the partition is suppressed and any separation between the partition and the inner surface of the housing due to the shrinkage of the potting composition is prevented. Further, is prevented from forming a weak bond portion between the partition and the inner surface of the housing. Further, if the entirety of the tip end of each projection is enclosed by the partition, any impact applied to that portion will be absorbed to prevent peeling off at the tip end of the projection.

We claim:
1. An artificial lung equipped with a heat exchanger comprising:
  a heat exchanger comprising:
    a heat exchange housing having:
      an internal wall;
      a heat-exchange fluid inlet;
      a heat-exchange fluid outlet;
      a first end portion; and
      a second end portion;

heat-exchange tubular means positioned in said heat exchange housing;

first and second partitions formed of a potting composition for respectively securing a first and a second end portion of said heat-exchange tubular means to said heat exchange housing in a fluid tight seal to partition an interior portion of said heat exchange housing into a heat-exchange fluid chamber in fluid communication with said heat-exchange fluid inlet and said heat-exchange fluid outlet, said heat exchange fluid chamber being defined by an outside surface of said heat exchange tubular means, said internal wall of said heat exchange housing and an internal surface of each of said first and second partitions, said internal surfaces of said partitions facing an interior of said heat exchange fluid chamber, and a blood chamber being defined by an internal surface of said heat-exchange tubular means;

a blood inlet and a blood outlet in fluid communication with said blood chamber;

a plurality of spaced apart projections formed on an inner surface of said first end portion of said heat exchange housing so as to project in a direction toward an end of said first end portion of said heat exchange housing and away from said second end portion of said heat exchange housing;

said first end portion of said heat exchange housing being positioned relative to said first partition so that an entirety of each of said plurality of spaced apart projections formed on said inner surface of said first end portion of said heat exchange housing are embedded in an annular area within said first partition such that a plurality of projection-free areas are formed between adjacent projections where said plurality of projections are not present, said projection-free areas enabling said potting composition to flow therethrough when said first partition is being formed from said potting composition; and an artificial lung comprising:
an artificial lung housing having a gas inlet and a gas outlet;
a bundle of gas-exchange hollow fibers positioned in said artificial lung housing;
partitions for respectively securing a first and a second end portion of said bundle of gas-exchange hollow fibers to said artificial lung housing in a fluid tight seal, to partition an interior of said artificial lung housing into a gas chamber in fluid communication with said gas inlet and said gas outlet, and a blood chamber defined in said gas-exchange hollow fibers; and
a blood inlet portion and a blood outlet portion in fluid communication with said blood chamber;
said first partition of said heat exchanger formed in said first end portion of said heat exchange housing facing and being connected to a given one of said partitions of said artificial lung.

2. An artificial lung equipped with a heat exchanger according to claim 1, wherein:
each of said first and second end portions of said heat exchange housing respectively have an annular shape and a diameter;
said first end portion of said heat exchange housing having a larger diameter than said second end portion; and
said plurality of projections are positioned within said larger diameter first end portion of said heat exchange housing.

3. An artificial lung equipped with a heat exchanger according to claim 1, wherein each of said projections has a reinforcement portion for connecting at least a part of a side surface of said projection to said inner surface of said first end portion of said heat exchange housing.

4. An artificial lung equipped with a heat exchanger according to claim 1, wherein said plurality of projections comprises an annular member inserted in said first end portion of said heat exchange housing.

5. An artificial lung equipped with a heat exchanger according to claim 1 wherein:
each of said first and second end portions of said heat exchange housing respectively have a different cross-sectional area;
said first end portion of said heat exchange housing having a larger cross-section area than said second end portion of said heat exchange housing; and
said plurality of projections are positioned within said first end portion of said heat exchange housing.

6. An artificial lung equipped with a heat exchanger according to claim 1, wherein said plurality of projections are positioned substantially at regular intervals in said annular area.

7. A fluid processing apparatus comprising:
a housing having:
an internal wall;
first and second end portions;
a first fluid inlet; and
a first fluid outlet;
a fluid processing tubular means positioned in said housing;
first and second partitions formed of a potting composition for respectively securing a first and a second end portion of said fluid processing tubular means to said first and second end portions of said housing in a fluid tight seal, to partition an interior of said housing into a first fluid chamber in fluid communication with said first fluid inlet and said first fluid outlet, said first fluid chamber being defined by an outside surface of said fluid processing tubular means, said internal wall of said housing, and an internal surface of each of said first and second partitions, said internal surfaces of said partitions facing an interior of said first fluid chamber, and a second fluid chamber being defined by an internal surface of said fluid processing tubular means;
a second fluid inlet and a second fluid outlet in fluid communication with said second fluid chamber;
a plurality of spaced apart projections formed on an inner surface of said first end portion of said housing so as to project in a direction toward an end of said first end portion of said housing and away from said second end portion of said housing; and
said first end portion of said housing being positioned relative to the first partition so that an entirety of each of said plurality of spaced apart projections formed on said inner surface of said first end portion of said housing are embedded in an annular area within said first partition, such that a plurality of projection-free areas are formed between adjacent projections where said plurality of projections are not present, said projection-free areas enabling said potting composition to flow therethrough when said first partition is being formed from said potting composition.

8. A fluid processing apparatus according to claim 7, wherein:
said annular area of said first partition, where said fluid processing tubular means is not present, is formed in a periphery of said first partition for securing said first end portion of said housing to said first end portion of said fluid processing tubular means; and
said plurality of projections formed on said inner surface of said first end portion of said housing being positioned in said annular area of said first partition.

9. A fluid processing apparatus according to claim 7, wherein:
each of said first and second end portions of said housing respectively have an annular shape and a diameter;
said first end portion of said housing having a larger diameter than said second end portion of said housing; and
said plurality of projections are positioned within said larger diameter first end portion of said housing.

10. A fluid processing apparatus according to claim 7, wherein:
said fluid processing tubular means comprises a heat-exchange tubular means; and
said fluid processing apparatus comprises a heat exchanger.

11. A fluid processing apparatus according to claim 7, wherein each of said projections has a reinforcement portion for connecting at least a part of a side surface of each projection to said inner surface of said first end portion of said housing.

12. A fluid processing apparatus according to claim 7, wherein said plurality of projections comprises an annular member inserted in said first end portion of said housing.

13. A fluid processing apparatus according to claim 7 wherein:
each of said first and second end portions of said housing respectively have a different cross-sectional area;
said first end portion of said housing having a larger cross-sectional area than said second end portion of said heat exchange housing; and
said plurality of projections are positioned within said first end portion of said heat exchange housing.

14. A fluid processing apparatus according to claim 7, wherein said plurality of projections are positioned substantially at regular intervals in said annular area.

* * * * *

UNITED STATES PATENT AND TRADEMARK OFFICE
CERTIFICATE OF CORRECTION

PATENT NO. : 5,192,499

DATED : March 9, 1993

INVENTOR(S) : SAKAI, Satoru et al

It is certified that error appears in the above-identified patent and that said Letters Patent is hereby corrected as shown below:

On the title page item, [56] References Cited:

Under "U.S. PATENT DOCUMENTS" insert,
    --3,722,695   3/1973   Sargent et al
      4,657,743   4/1987   Kanno
      4,376,095   3/1983   Hasegawa--.

Under "FOREIGN PATENT DOCUMENTS" insert,
    --0 297 410   1/1989   European Patent Office--.

Column 1, line 59, "well" should be --will--.

Signed and Sealed this

Twentieth Day of December, 1994

Attest:

BRUCE LEHMAN

*Attesting Officer*    *Commissioner of Patents and Trademarks*